United States Patent
Peoples, Jr.

[11] Patent Number: 6,098,892
[45] Date of Patent: Aug. 8, 2000

[54] DEVICE FOR CONVERSION FROM A PHARMACEUTICAL IDENTIFICATION NUMBER TO A STANDARDIZED NUMBER AND METHOD FOR DOING THE SAME

[76] Inventor: Max J. Peoples, Jr., 2737 Cooper Ridge Rd., Columbus, Ohio 43231

[21] Appl. No.: 09/085,279

[22] Filed: May 27, 1998

Related U.S. Application Data
[60] Provisional application No. 60/048,124, May 30, 1997.

[51] Int. Cl.[7] .................. G06K 7/10; G06K 5/04
[52] U.S. Cl. ............... 235/494; 235/462.01; 235/462.07; 235/462.12
[58] Field of Search ................. 235/462.01, 462.07, 235/462.12, 375, 380, 494

[56] References Cited

U.S. PATENT DOCUMENTS

| | | | |
|---|---|---|---|
| 4,146,175 | 3/1979 | Daboub et al. | 235/462 |
| 4,415,802 | 11/1983 | Long | 235/382 |
| 4,476,381 | 10/1984 | Rubin | 235/375 |
| 4,788,419 | 11/1988 | Walters et al. | 235/381 |
| 4,835,372 | 5/1989 | Gombrich et al. | 235/375 |
| 5,164,575 | 11/1992 | Neeley et al. | 235/472.01 |
| 5,227,617 | 7/1993 | Christopher et al. | 235/462 |
| 5,272,318 | 12/1993 | Gorman . | |
| 5,374,813 | 12/1994 | Shipp | 235/375 |
| 5,381,487 | 1/1995 | Shamos | 382/2 |
| 5,382,779 | 1/1995 | Gupta | 235/383 |
| 5,401,110 | 3/1995 | Neeley | 408/621 |
| 5,468,110 | 11/1995 | McDonald et al. | 414/273 |
| 5,479,588 | 12/1995 | Sawada et al. | 395/117 |
| 5,481,098 | 1/1996 | Davis et al. | 235/462 |
| 5,496,117 | 3/1996 | Sawada et al. | 400/61 |
| 5,502,944 | 4/1996 | Kraft et al. | 33/55 |
| 5,508,499 | 4/1996 | Ferrario | 235/375 |
| 5,510,603 | 4/1996 | Hess et al. | 235/454 |
| 5,528,021 | 6/1996 | Lassus et al. | 235/380 |
| 5,550,734 | 8/1996 | Tarter et al. | 364/401 |
| 5,592,374 | 1/1997 | Fellegara et al. | 395/203 |
| 5,597,995 | 1/1997 | Williams et al. | 235/375 |
| 5,739,518 | 4/1998 | Wang | 235/454 |

*Primary Examiner*—Michael G Lee
*Assistant Examiner*—Douglas X. Rodriquez
*Attorney, Agent, or Firm*—Rader, Fishman, Grauer & McGarry

[57] ABSTRACT

A device and method is provided for converting product-specific identification numbers associated with bar code indicia on pharmaceutical products to an industry standard identification number. The process involves reading a bar code indicia, converting the indicia into an input string and standardizing the input string by means of adding or subtracting characters in accordance with rules based on the bar code type and length of the input string. By means of the invention pharmaceutical products of two different sources may be compared to determine if they contain the same drug as determined by the standard identification number. The device can include a removable member for interchanging and updating bar code indicia information rather than reprogramming the device.

51 Claims, 11 Drawing Sheets

Code 39

TEST-SHEET

Code 2 of 5

123456

Code 11

11223344

UPC-A          5 addenda 031323120786        56098

MSI †

44332211

TRUNCATED UPC-A/EAN-13 SYMBOLS
(200 digs)

3141592665358 (2)

PDF417

Welch Allyn . . . (70 chars)

Codabar

0013557900

Interleaved 2 of 5

1234567890

Matrix 2 of 5

6543210

Code 128

Code 128

EAN 13

9780330290951

Plessey †

9876

FULL-HEIGHT UPC-A/EAN-13 SYMBOLS
Library of Congress CIP Data 978007911720 (5)

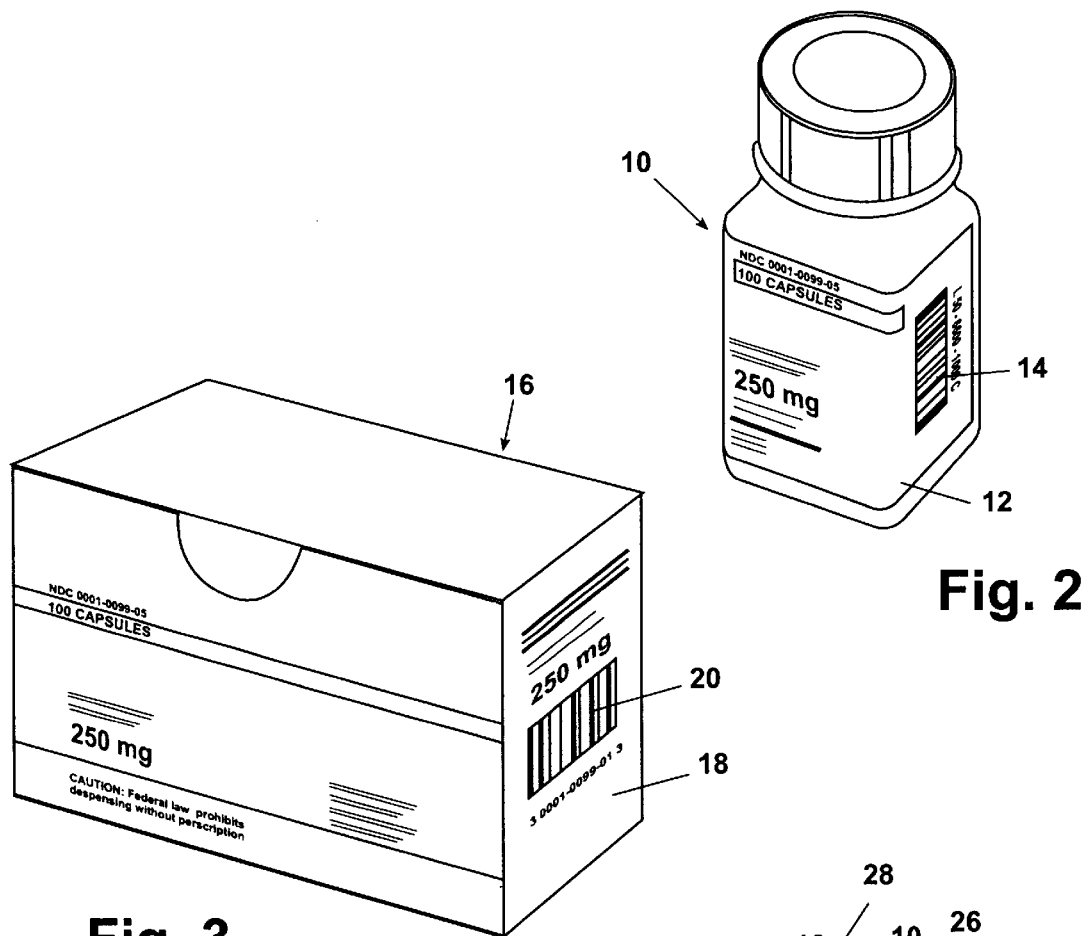
Fig. 2
Fig. 3
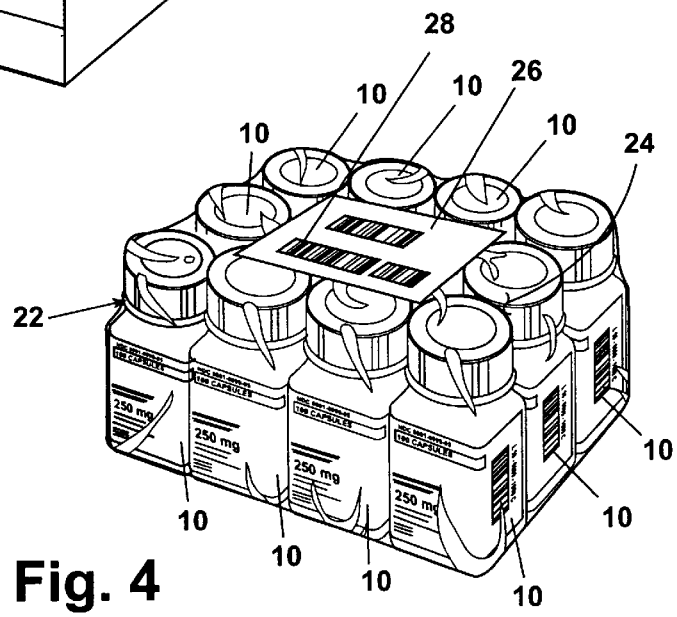
Fig. 4

DEVICE FOR CONVERSION FROM A PHARMACEUTICAL IDENTIFICATION NUMBER TO A STANDARDIZED NUMBER AND METHOD FOR DOING THE SAME

CROSS-REFERENCE TO RELATED APPLICATIONS

This application claims priority on U.S. application Ser. No. 60/048,124, filed May 30, 1997.

BACKGROUND OF THE INVENTION

1. Field of the Invention

The invention relates to a device and method for converting a product-specific identification number to an industry standard identification number. More specifically, the invention relates to a device and method for converting a bar code displayed on a package for pharmaceuticals into a standardized code which is known throughout the pharmaceutical industry.

2. Description of Related Art

Universal Product Code (UPC) symbols are displayed on a myriad of products throughout the country. Often, the UPC symbol is displayed in a "bar code" format, whereby an intermittent pattern of alternating black and white vertical lines of varying widths signifies a string of alphanumeric characters. Bar codes serve as a language which functions to place the string of characters into a machine-readable form. In addition, bar codes have a number of formats which typically must be determined before a machine can read a bar code. FIG. 1 shows examples of different types of bar codes with the generally-accepted name of the type of bar code shown directly above the bar code.

UPC symbols, in the form of bar codes, are commonly displayed on all kinds of products, including those in the pharmaceutical industry such as medicine containers. FIGS. 2–5 show examples of medicine containers which have been provided with UPC symbols by a product source, such as a manufacturer or distributor. FIG. 2 shows a bottle 10 having a label 12 provided with bar code indicia 14 thereon. FIG. 3 shows a box 16 having a sidewall 18 provided with bar code indicia 20 thereon. FIG. 4 shows a shrink wrapped package 22 of multiple bottles 10 having an upper surface 24 on which a label 26 provided with bar code indicia 28 thereon has been affixed. FIG. 5 shows a carton 30 having a label 32 provided with bar code indicia 34 thereon.

Bar codes are typically read by a device called a "scanner." An example of a system which includes a scanner is shown in FIG. 6. The system, shown generally by reference numeral 36, comprises a computer 38 and a scanner 40 interconnected by a conduit 42. The computer 38 generally comprises a processing unit 44, a keyboard 46 and a monitor 48. It will be understood that the monitor 48 and the processing unit 44 are interconnected in a manner well known in the art. The conduit 42 comprises a Y-shaped cable having first, second and third portions 50, 52 and 54, respectively, each provided with a suitable connector 56 at a distal end.

The scanner 40 is typically interconnected intermediate the keyboard 46 and the processing unit 44 by the conduit 42. For example, the connector 56 on the first portion 50 is interconnected to a suitable socket (not shown) on the scanner 40. The connector 56 on the second portion 52 is interconnected to a suitable socket 58 on the keyboard 46. The connector 56 of the third portion 54 is interconnected to a suitable socket (not shown) on the processing unit 44.

Thus, signals can be provided to the processing unit 44 by either the keyboard 46 through the portions 50–54 or by the scanner 40 through the portions 50 and 54. FIG. 7 shows the operation of the scanner 40. The scanner 40 typically includes an illumination-emitting device therein, such as a laser or intense light, which is actuatable by a trigger (not shown). When the trigger is depressed, a beam 60 is oscillated across a bar code 62 desired to be read. The bar code 62 is converted to an alphanumeric signal by the scanner 40 and sent through the conduit 42 to the processing unit 44. Because the scanner 40 is interconnected intermediate the keyboard 46 and the processing unit 44 and is able to generate alphanumeric characters, the scanner 40 acts as a "second keyboard," providing alphanumeric input to the processing unit 44.

As shown in FIGS. 2–5, bar codes in the form of UPC symbols are marked on packaging for medicine and other pharmaceuticals. With continuing pressure to reduce health care costs there is a need to use technology to improve the quality and accuracy of pharmaceutical distribution. The National Drug Code (NDC) was developed as a universal identification system for pharmaceutical products distributed in the U.S. Since 1969, the Food and Drug Administration (FDA) has required that all drug products be identified clearly with the NDC, which provides pharmaceutical products with a unique all-numeric system identifying the pharmaceutical source, product and package size. Because the industry uses the NDC to order, track and report on pharmaceutical products, bar coding of this number has provided a faster and more accurate way to move both products and information.

The NDC for prescription pharmaceuticals is the single basic identifier for all forms of pharmaceutical products in the health industry. Pharmacy computer systems, third-party prescription claims processing, and sale tracking, reporting and industry support services typically use the NDC to identify, describe and pay for pharmaceutical services. For pharmacy providers, legislation now mandates the use of the NDC for all Medicaid claims. The Department of Justice and the Drug Enforcement Administration require monthly reporting of all incoming and outgoing controlled substance transactions and inventories on a system which mandates use of NDC numbers. From drug manufacturer to wholesaler to drug provider, computer systems are often required to depend on NDC numbers for identifying what is being ordered, paid, returned and credited. It is a proven method of enhancing the efficiency and accuracy of pharmaceutical distribution.

The NDC, by federal regulation, is a 10-digit numeric code preceded with the letter N or letters NDC. It consists of three numeric fields of information: a source identification field, a product identification field, and a trade package field. The FDA assigns the labeler portion of the code, while the labeler assigns the product identification and trade package portions according to format standards.

The FDA originally assigned the source identification field as four digits. starting at 0002. The system was designed not to exceed a source identification field of 0999. When it became apparent to the FDA that the number of product sources applying for labeler codes would exceed 0999, they reformatted the source I.D. field to comprise a five-digit numeric field beginning with 10000.

The product identification and trade package fields together comprise five digits, with the product identification field being three or four digits and the trade package field being two or one.

The NDC is presented in one of three formats: 4-4-2,5-3-2 or 5-4-1 referred to in order of the above-identified three fields. The first field of four or five numbers corresponds to the source identification field. The next field of three or four numbers corresponds to the product identification field. The final field of one or two numbers corresponds to the trade package field.

Whenever an NDC is printed, all leading, imbedded and trailing zeros must be included. Each of the three fields are typically separated by a hyphen when printed in a human readable form, for example, 51999-432-10 for a 5-3-2 NDC number.

In their catalogs and on price lists, manufacturers and labelers are encouraged to include NDC numbers for each listed item. Labelers are typically urged to discontinue use of internal or traditional list, order or product numbers, as these identifiers are not generic to the pharmaceutical industry.

Because the NDC is the single basic means of product identification for all pharmaceutical products, it is desirable to have the NDC numbers encoded into a bar code and labeled onto products. Therefor, drug manufacturers and labelers are urged to identify their drug products with an NDC and to encode this number in bar code formats. However, there are many different bar code types as shown by example in FIG. 1 and a growing number of applications for each. Problems have arisen in that the various bar code types have different character lengths which do not correspond to the ten-digit NDC number.

SUMMARY OF THE INVENTION

The present invention relates to a device and method for converting a productspecific identification number associated with a pharmaceutical drug to an industry standard identification number known as an NDC format output. In practice, product sources use one of several different types of bar code indicia including UPC 10 and 15 haracter codes, Code 39, Code 128, Interleaved 2 of 5, and two- and three-dimensional bar codes. The present invention reads the bar code indicia with a scanner, converts the bar code indicia into an input string of a first length, manipulates the input string into a standardized first string so that the length of the first string equals the fixed length of the standardized string, and then sends the first string to a processing unit.

The process of manipulating the bar code indicia requires identifying if the bar code indicia is of a predetermined type, eliminating check characters from the input string, and eliminating other non-standard characters from the input string. For most of the bar code indicia, a leading zero is added to the standardized first string, followed by at least a portion of the input string. In some cases, a number of the characters of the input string are replaced by a substitute string of characters. In other cases, particularly where more than ten characters are involved, only a portion of the input string is copied to the standardized first string.

The present invention also teaches a method for verifying that a first and second bar code indicia are identical so that an individual such as a pharmacist or pharmacy technician may determine if two products from two different sources, actually consist of the same pharmaceutical product. The process involves reading a first bar code indicia, converting the first bar code indicia into a standardized first string and then sending the first string to a processing unit such as a computer where it is stored. Then, a second bar code indicia is read, converted into a standardized second string, and stored in the processing unit. Then the first and second standardized strings are compared. If the strings match a confirmation signal may be generated. Alternatively, if the strings don't match an alarm signal may be generated.

In another aspect, the invention relates to a scanner for reading bar code indicia comprising a housing having a port, a scanning mechanism located in the housing in register with the port adapted to read the bar code indicia into the memory, a first controller mounted in the housing for operating the scanning mechanism interconnected with one of a socket and a connector, and a member mounted to the housing having a second controller interconnected with the other of the socket and the connector, the socket adapted to be removably mounted to the connector for data transfer between the first controller and the second controller whereby when the socket is mounted to the connector, the first and second controllers can interchange data regarding the bar code indicia to be read by the scanner.

The member is preferably removably mounted to the housing whereby the socket and connector are disconnected when the member is removed from the housing. The second controller can contain a memory having data required by the first controller for interpreting the bar code indicia read by the scanner.

BRIEF DESCRIPTION OF THE DRAWINGS

The invention will now be described with reference to the drawings wherein:

FIG. 2 is a perspective view of a medicine bottle having a bar code thereon;

FIG. 3 is a perspective view of a small box having a bar code thereon;

FIG. 4 is a perspective view of a shrink wrapped package of multiple medicine bottles having a bar code thereon;

DESCRIPTION OF THE PREFERRED EMBODIMENTS

Figure 1:
FIG. 1 is a view of several different types of bar codes shown with the name of the type of bar code shown therewith.
Figure 1:
Figure 1:
Figure 1:
Figure 1:
Figure 1:
Figure 1:
Figure 1:
Figure 1:
Figure 1:
Figure 1:
Figure 1:
Figure 1:
Figure 1:
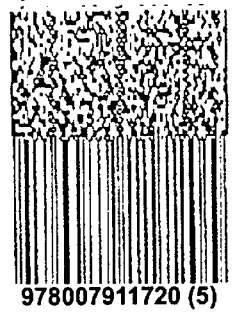
Figure 6:
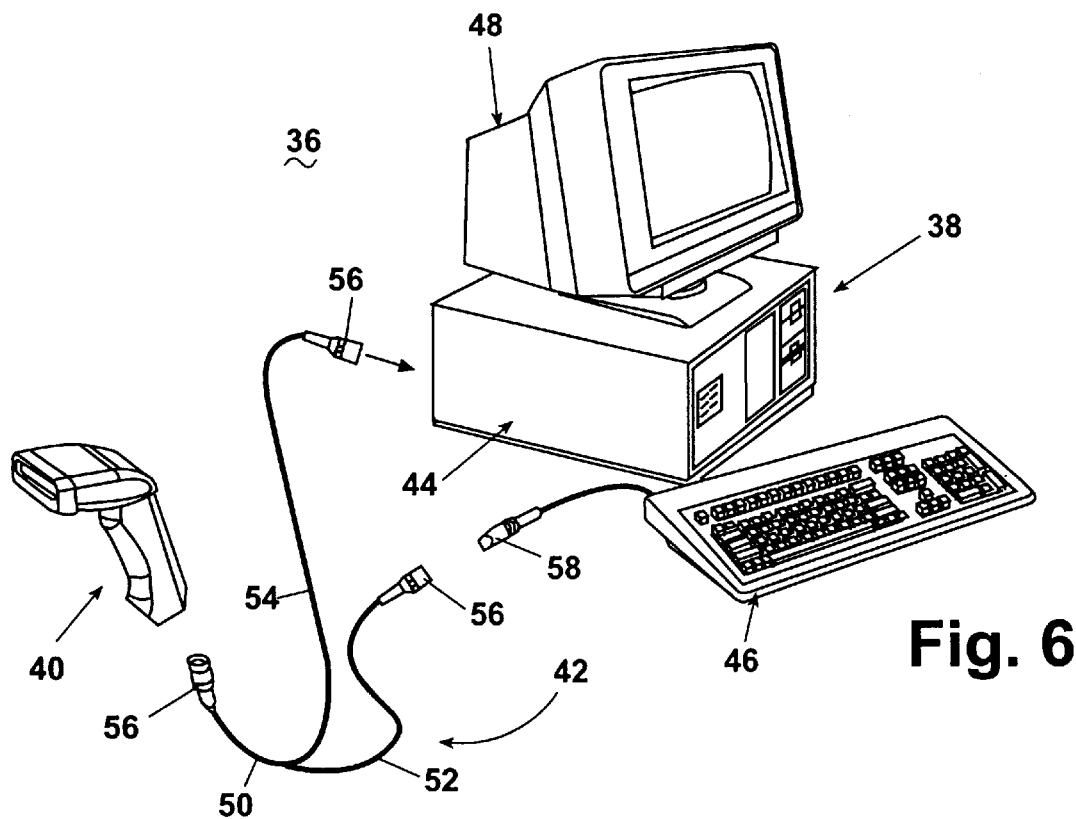
FIG. 6 is a perspective view of a typical computer system incorporating a scanner therein.
Figure 5:
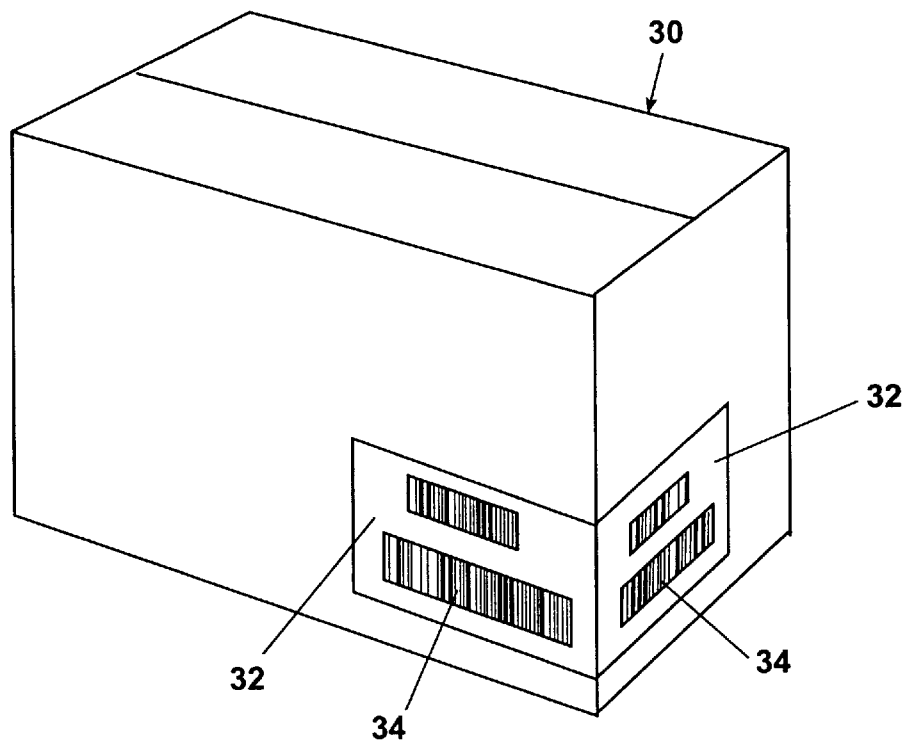
FIG. 5 is a perspective view of a large carton having a bar code thereon.
Figure 9:
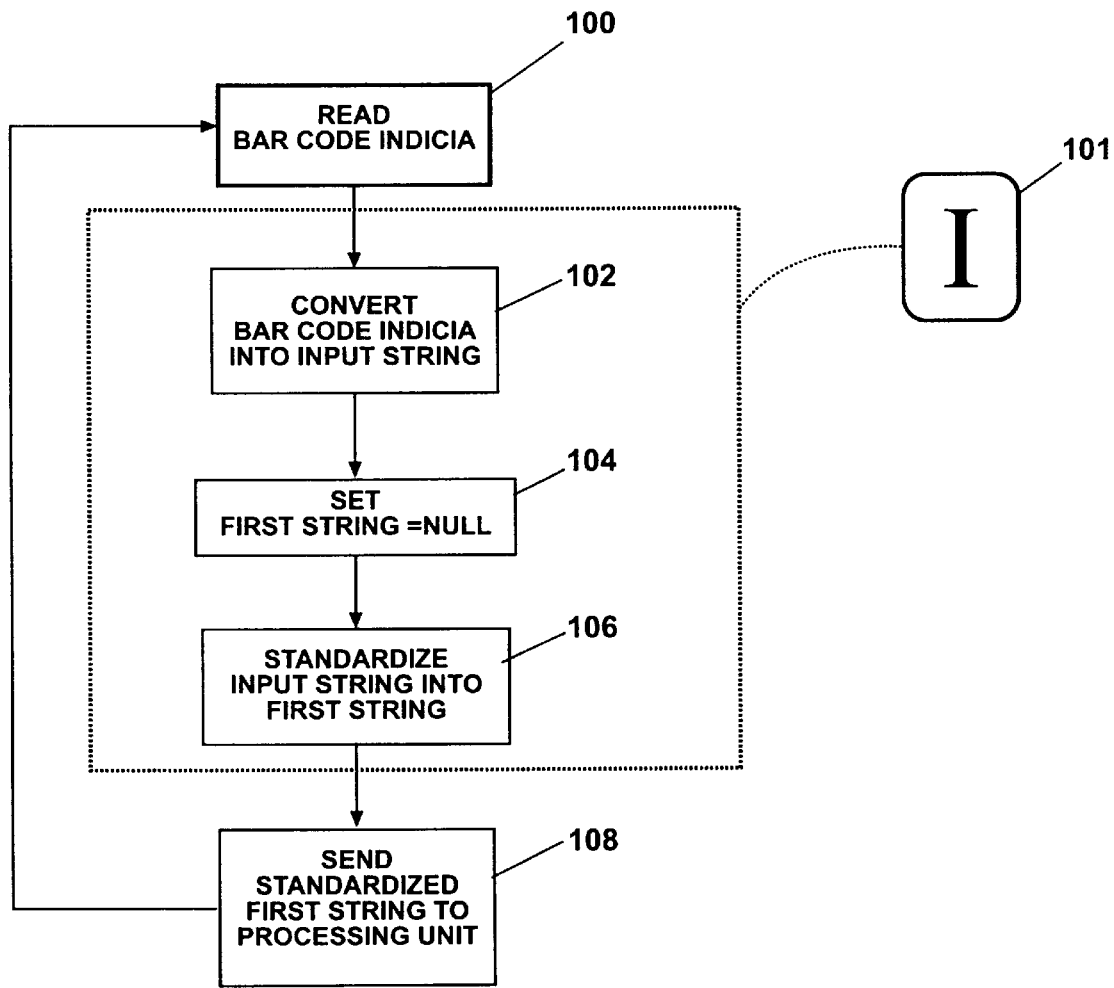
FIG. 9 is a flow chart illustrating the method of converting a bar code to a standardized NDC number.

The present invention comprises the converting of a bar code of any of the formats shown in FIG. 1 to a standardized 11-digit NDC number while simultaneously ensuring accurate entry of data relating to the pharmaceutical product into a computer system. As shown in FIG. 9, the first basic step 100 involves reading a bar code in the form of machine-readable data. Such a bar code is typically found on the source's medication container. Bar codes on a source's bulk medication container can contain a bar code in a UPC symbol format or any of the other formats shown in FIG. 1. The manipulating of the data contained in the bar code into an NDC output format 101 comprises a step 102 of converting a bar code indicia into an input string, a step 104 of setting the first string to null, and a step 106 of standardizing the input string into a first string. Finally, as shown in step 108, the NDC output format 101 of the manipulated bar code is sent to a processing unit on a computer 38, as illustrated in FIG. 6. It will be understood that, although a particular scanning unit 40 and computer system 38 is disclosed in the drawings, any type of scanning unit having an internal or external connection to a processor can be used without departing from the scope of this invention. This includes a scanning device having all processing and memory elements contained in a unitary configuration or separate components, as shown in FIG. 6.

Figure 10:
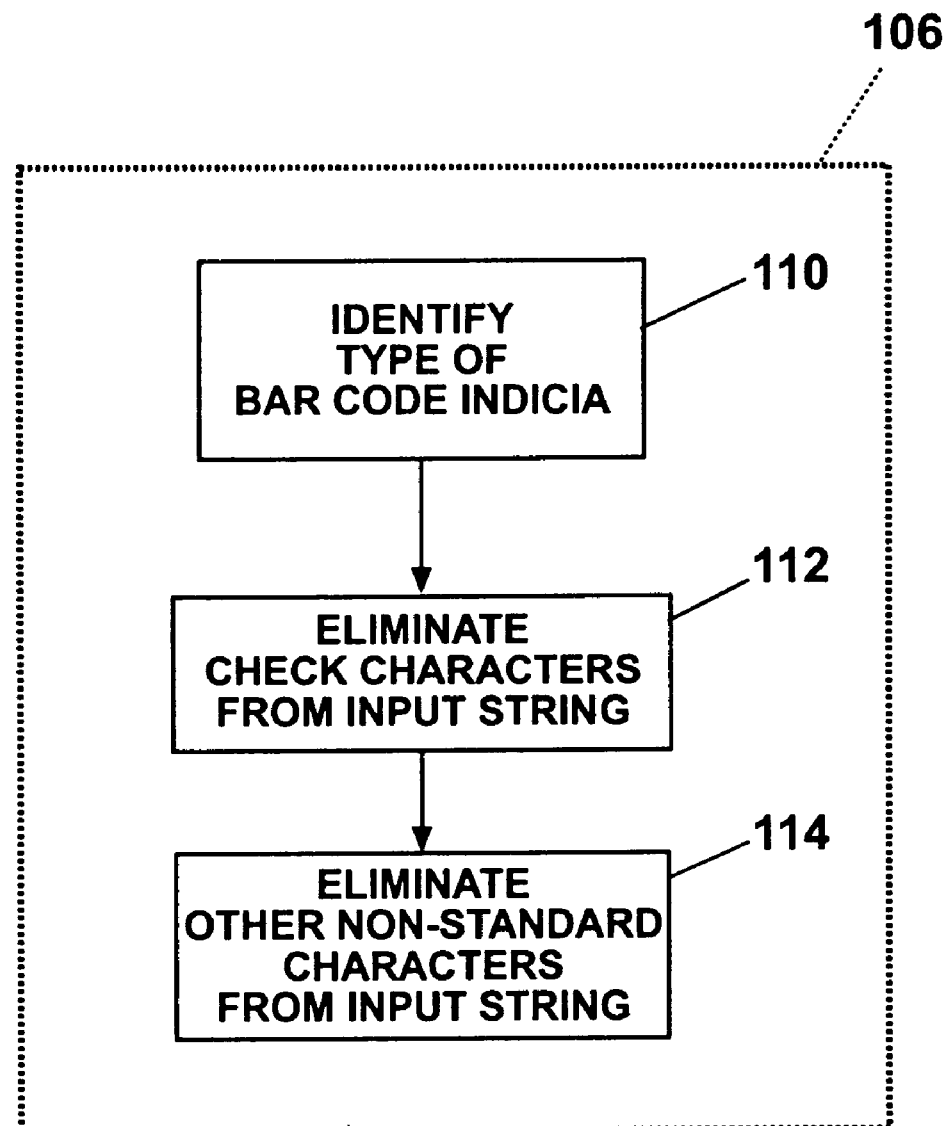
FIG. 10 is a flow chart illustrating the process of standardizing an input string into a first string.

The step 106 of standardizing an input string into a first string may be broken down into a number of additional steps illustrated in FIG. 10. First, as shown by step 110, the type of bar code must be identified. Second, as shown by step 112, any check digits present in the alphanumeric string read by the baothede must be eliminated. Third, any other digits not contained in an 11-digit NDC number must be eliminated as shown by step 114.

Figure 11:
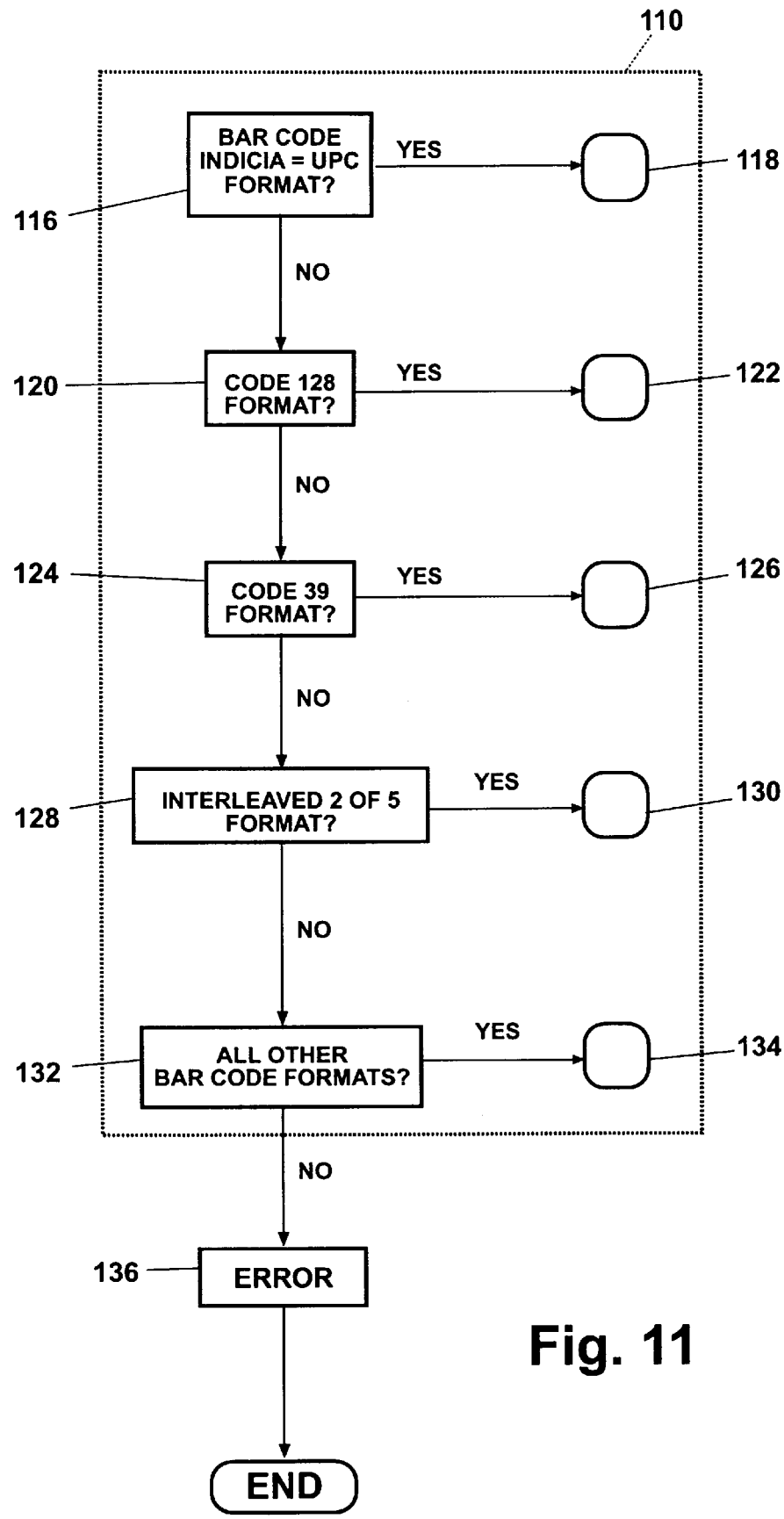
FIG. 11 is a flow chart illustrating the process for eliminating non-standard characters from the input string.

The following paragraphs outline the rules for converting a bar code into an NDC number depending upon the type of bar code read by a scanning device in accordance with a further breakdown of steps 110, 112, and 114. FIG. 11 in an expansion of step 110, wherein it will be understood that the scanning device has the ability to recognize a particular type of bar code.

Figure 13:
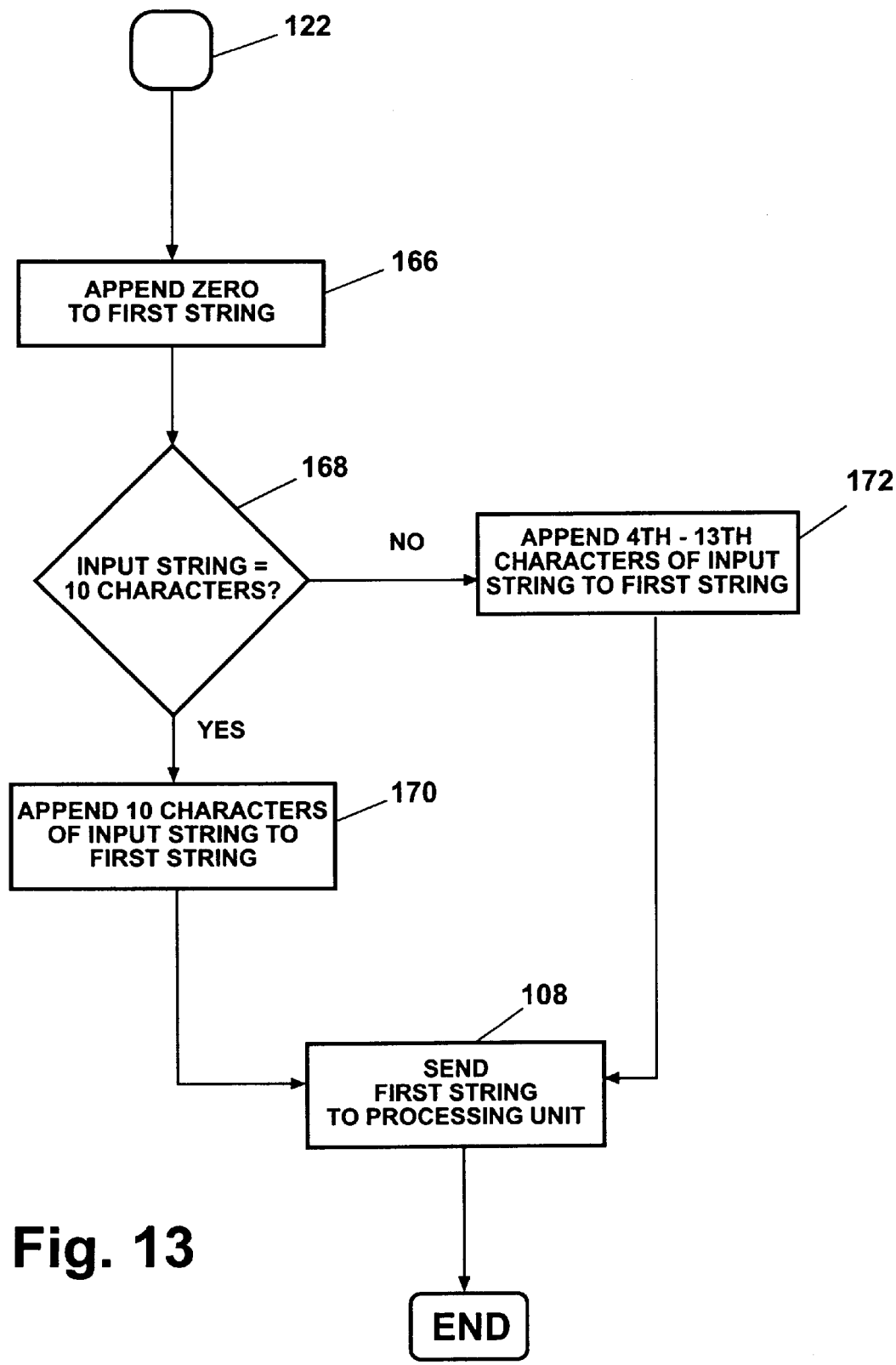
FIG. 13 is a flow chart illustrating the process of standardizing a bar code of Code 128 format.
Figure 14:
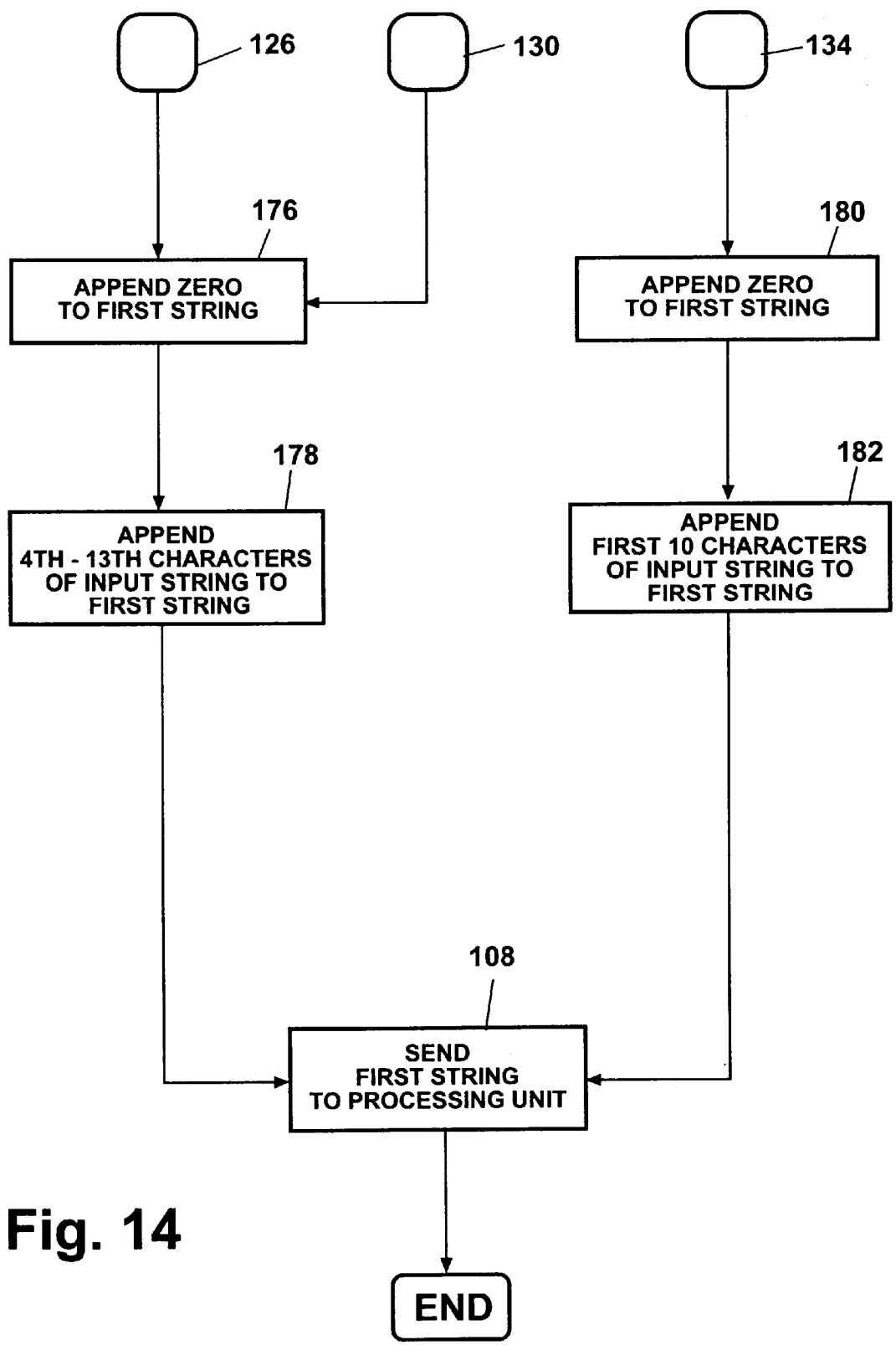
FIG. 14 is a flow chart illustrating the process of standardizing a bar code of Code 39, Interleaved 2 of 5, and other bar code formats.

At step 116, the device determines if the bar code indicia is equal to UPC format. If it is, then the formatting rules for the UPC format are followed at block 118 as illustrated in greater detail in FIG. 12. Alternatively, at step 120, if the bar code indicia is Code 128 format then the formatting rules for the Code 128 format are followed at block 122 as illustrated in greater detail in FIG. 13. If the bar code indicia is instead of Code 39 format as determined at step 124, then the formatting rules for the Code 39 format are followed at block 126 as shown in greater detail in FIG. 14. At step 128, the device determines if the bar code Indicia is of Interleaved 2 of 5 format. If so, then the formatting rules of block 130 are followed as also shown in FIG. 14. Finally, at step 132 the device determines if the bar code indicia are of any other recognized format. If so, then the formatting rules represented by block 134 are followed. Thus, the device calls upon one of the following format rules represented by blocks 118, 122, 126, 130, or 134, respectively, depending upon the type of bar code read. If the particular type of bar code cannot be recognized, the system returns an error at point 136 and the process ends.

Figure 12:
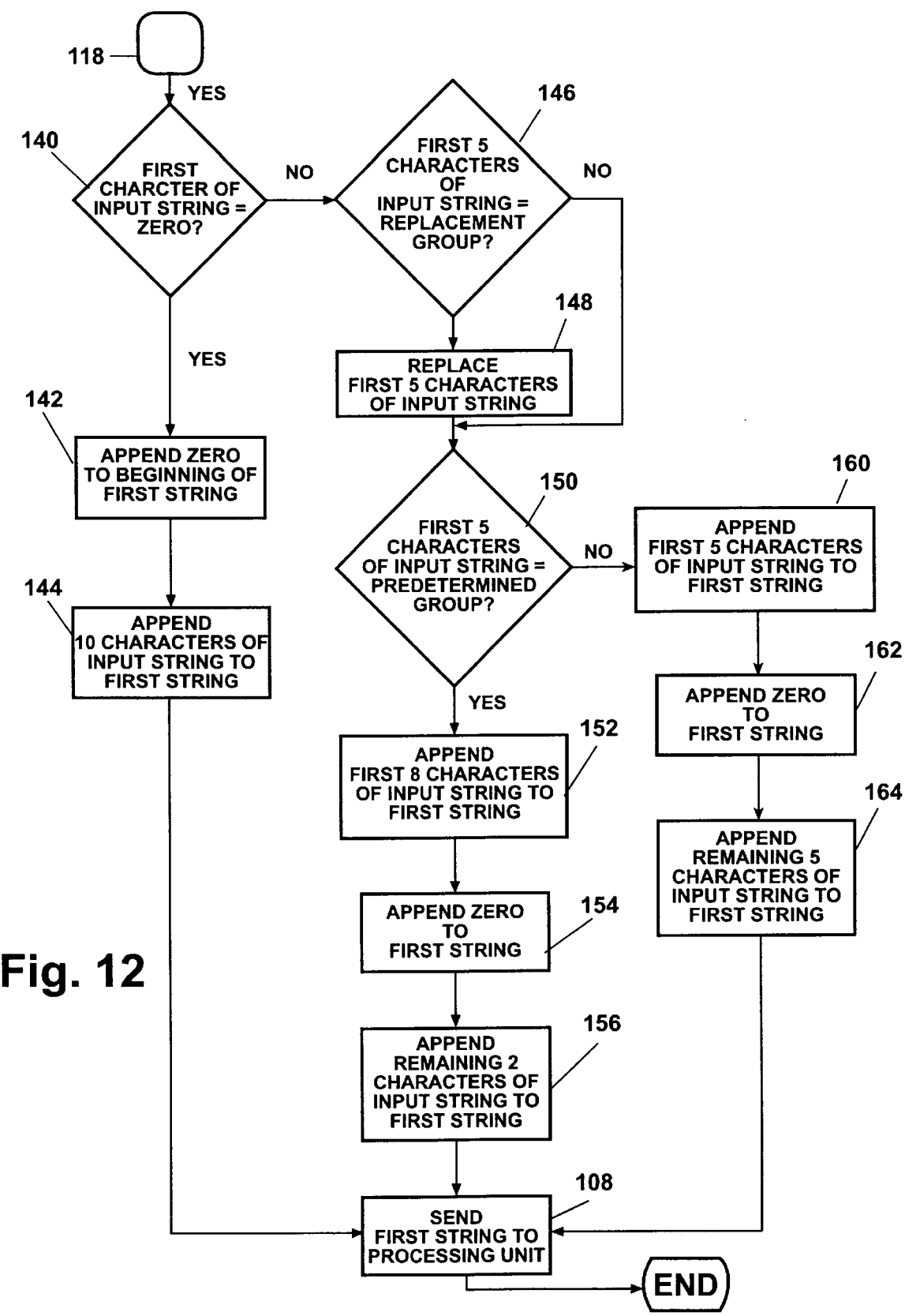
FIG. 12 is a flow chart illustrating the process of standardizing a bar code of UPC format.

For a UPC formatted bar code represented by block 118, the scanner reads the bar code at step 100 and converts it into an input string of the ten digits contained in a UPC bar code at step 102. Then to standardize the input string into a first string in a break down of steps 112 and 114, the specific approach illustrated in FIG. 12 is utilized. The first or lead character of the inputted string is identified at decision point 140. If the first character is a zero, then a zero is inserted at the beginning of the bar code at 142 and the ten characters of the alphanumeric string are appended thereto at 144 and sent to the process unit as shown by step 108. If the lead character is not a zero, then at decision point 146 the device determines if the first five characters of the input string are a replacement group. If the answer is no, then the device determines at decision point 150 if the first five characters in the alphanumeric string read by the scanning device are a predetermined group of, such as, but not limited to, 59911, 51875, 59930, 59762, 58634, 51672, 59366, or 59772. If the answer is yes, then the device sends the first eight digits of the inputted alphanumeric string from the bar code as shown by point 152, then a zero as shown by point 154, and then the remaining two characters of the alphanumeric string as shown by point 156 to create the first string. Then the first string is sent to the processing unit as shown by point 108.

If the first five characters of the input string comprise a replacement group at decision point 146, then the first five digits must be replaced with a substitute string as shown at point 148. For example, it has been found that if the first five digits are in the group of, but not limited to, 28176, 12899 and 47228, then the device must substitute the strings 51285, 55953 and 55053, respectively. This substitution is made for the purpose of converting a particular source's bar code to that source's NDC number. It will be understood that additional substitute NDC numbers can be provided in a database or other look-up table as required. Then, the process continues to decision step 150 as discussed above.

For UPC symbols wherein the first five characters of the input string are not a predetermined group at decision point 150, the scanning device will send the first five characters of the inputted string as shown at point 160, then a zero as shown at point 162, and then the remaining five characters of the UPC string as shown at point 164. Then the first string is sent to the processing unit as shown by point 108. Thus, in all cases, an 11-digit NDC number is produced and transmitted to the processing unit. For a code 128 formatted bar code represented by block 122, the scanner reads the bar code at step 100 and converts it into an input string. As shown in FIG. 13, for bar codes in Code 128 format, the bar codes typically produce either 10 or 15 alphanumeric characters when read by a scanning device. For a Code 128 bar code with 10 characters, the scanning device transmits a zero shown at step 166 followed by the ten digits of the inputted string. At decision point 168 the device confirms that the input string has 10 characters and then appends the ten characters of the input string to the first string at step 170. The first string is then sent to the processing unit as shown by step 108.

For bar codes in Code 128 format with 15 characters, the scanning device transmits a zero as shown at step 166, confirms that the input string has 15 characters at decision point 168 and then appends ten sequential characters of the input string beginning with the fourth character and ending with the thirteenth character as shown at step 172. The first string is then sent to the processing unit as shown by step 108.

For bar codes in Code 39 format represented by block 126, the scanner reads the bar code at step 100 and converts it into an input string. For bar codes in Code 39 format, the inputted alphanumeric string typically produces fifteen characters. As shown in FIG. 14, the scanning device transmits a zero as shown at point 176 in FIG. 14, followed by ten characters selected from the input alphanumeric string comprising the fourth through thirteenth characters therefrom as shown at point 178. The first string is then sent to the processing unit as shown by step 108.

For bar codes in Interleaved 2 of 5 format, represented by block 130, the bar codes typically produce a 14-character alphanumeric string. For these types of bar codes, the scanner reads the bar code at step 100 and converts it into an input string. The scanning device transmits a zero as shown at step 176, followed by the fourth through thirteenth characters in the inputted alphanumeric string as shown at point 178. The first string is then sent to the processing unit as shown by step 108.

For all other bar codes, represented by block 134 in FIG. 14, the scanning device transmits a zero as shown at step 180, followed by the first ten characters of the inputted alphanumeric string as shown by step 182 to form the 11-digit NDC number. Once again, the first string is then sent to the processing unit as shown by step 108.

A second embodiment of a method according to this invention compares a bar code on a source's pharmaceutical container with a bar code on a patient's prescription bottle, receipt or prescription which was printed by a pharmacy or doctor's office to verify that a correct prescription was dispensed.

Figure 15:
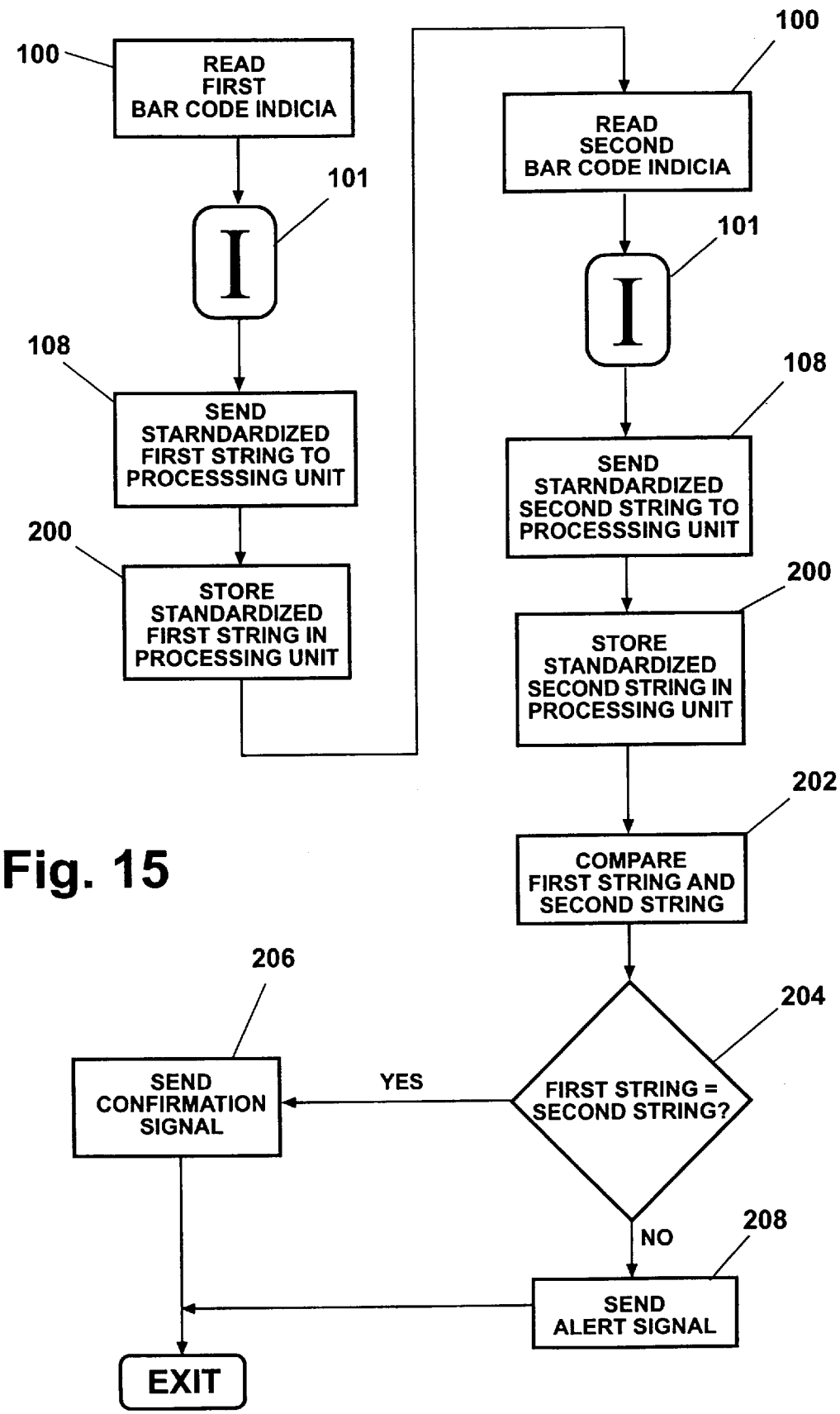
FIG. 15 illustrates a second method of comparing two bar code indicia.

As illustrated in FIG. 15, the second embodiment of a method comprises the step 100 of reading a first bar code from a first label. The first bar code is manipulated into an NDC output format or number 101 by the first embodiment of the method outlined above. The NDC number 101 is transmitted to the processing unit as shown by step 108 described above. The number 101 is then stored therein as shown at point 200. A second bar code is read from a label from a different container or prescription bottle or receipt by means of step 100. The second bar code is also manipulated into an NDC number 101 and transmitted to the processing unit and stored therein as shown by the repetition of steps 108 and 200. The first and second manipulated NDC numbers 101 are then compared at step 202 to determine whether they match. As shown at decision point 204, if the first and second NDC numbers 101 match, a confirmation signal 206 is sent. Alternatively, an alert signal 208 is sent.

It will be understood that the processing unit can be located in a conventional computer workstation as described in the Background section or, alternatively, located in the scanning unit itself. For the latter option, greater convenience can be had by the operator because the scanning mechanism and processing unit are located in a single housing.

Thus, bar codes in varying formats from different sources can be converted into a standard NDC number and compared to determine whether the pharmaceutical products identified in each of the first and second bar codes are indeed the same product. It can thereby be verified that a patient has received a correct product and dosage. Otherwise, the pharmacist or pharmacy technician will receive an alarm before an incorrect product is dispensed.

It is contemplated that the scanner employed in connection with this invention be any type of suitable scanner capable of reading bar code indicia into a processing unit. Further, it is also contemplated that the scanner employed in connection with this invention be capable of reading all of, but not limited to, the bar code types displayed in FIG. 1. These bar codes include typical one-dimensional bar codes such as code 39 and code 128, two-dimensional bar codes such as PDF 417, and full height and truncated UPC-A-EAN-13 symbols as shown in FIG. 1. Further, it is also contemplated that the scanner can read new types of bar codes such as three-dimensional bar codes by means of an imaging mechanism incorporated into the scanner or other means currently known or developed.

Figure 7:
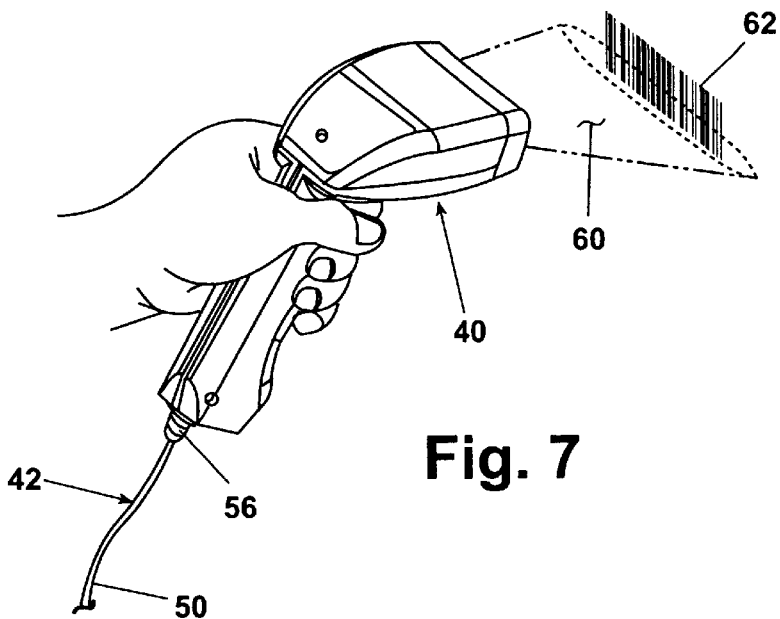
FIG. 7 is a perspective view of a prior art scanning device shown reading a typical bar code.

This invention also addresses the problem of updating a scanner's memory to reflect recent changes or additions to frequently changing bar code conversion information or routines stored in the scanner. Scanning devices, such as that shown as 40 in FIGS. 6–7, are typically provided with a memory chip (not shown) therein having a bank of random access memory (RAM) therein. Critical information, such as bar code recognition software and alphanumeric output programs, is loaded into the RAM and stored. Pharmaceutical suppliers and vendors often load information pertaining to recognition of specific bar code content as well, such as software which recognizes particular bar codes or a data bank of common bar codes.

As new bar code information becomes available, it must be downloaded into the RAM of the scanner 40. This process can be tedious, especially if a large volume or several smaller volumes of changes are required.

Figure 8:
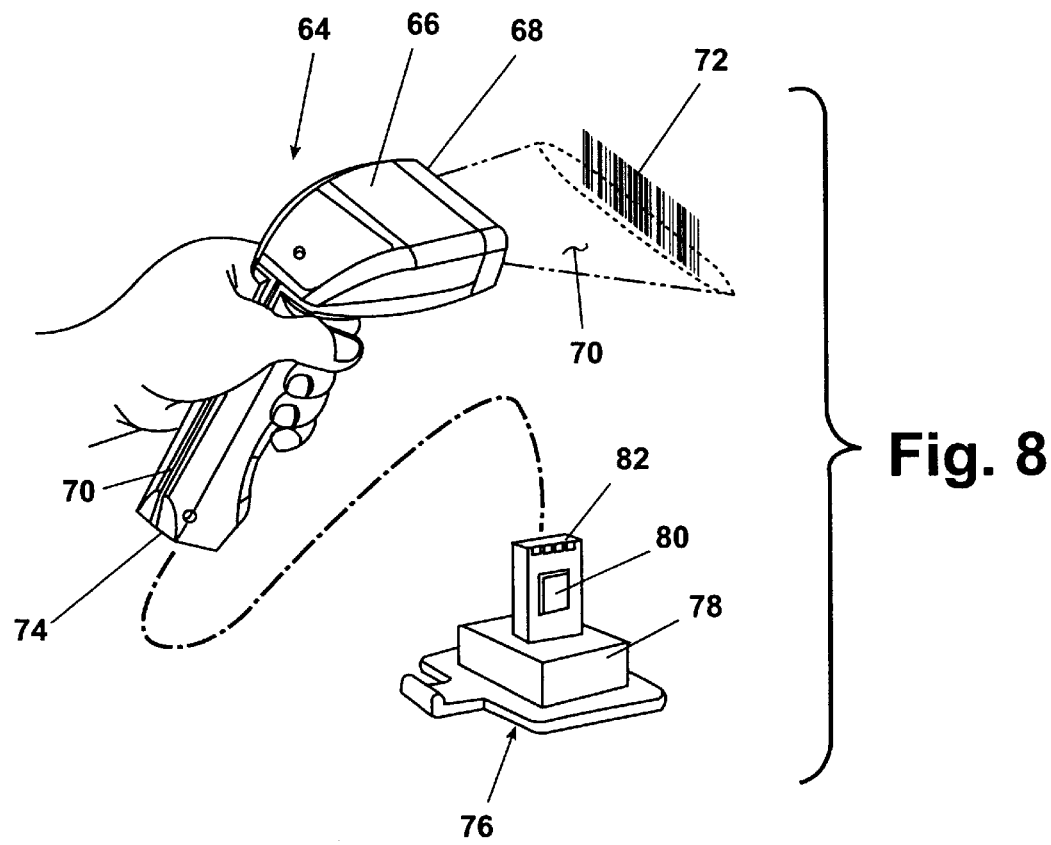
FIG. 8 is a perspective view of an improved scanning device according to the invention.

FIG. 8 shows an example of improved scanner 64 according to the invention which comprises a housing 66 having a laser port 68 and a handle 70. The scanner 64 is shown emitting a beam 70 over a bar code 72 as is conventionally done in the art. A distal end 74 of the handle 70 is provided with a removable panel 76 thereon. The panel 76 includes a substrate 78 which mounts a orthogonally-extending removable circuit 80 having a connector 82 thereon. The panel 76 is adapted to be inserted into the handle 70 and interconnected to the internal circuitry of the scanner 64 via the connector 82. The removable panel 76 can be positioned at any suitable location on the scanner 64 so that the panel 76 can be easily removed and does not interfere with any required connections to external components.

The circuit 80 is preferably a removable integrated circuit chip which can be removed and replaced with a new chip having any new bar code data stored thereon in addition to any older information to be retained. Thus, when new information becomes available, it can be mass produced in a new chip which thereby can be mounted to the panel 76 and inserted into the scanner 64. Thus, the need for a complicated reprogramming procedure for the scanner is eliminated.

While particular embodiments of the invention have been shown, it will be understood, of course, that the invention is not limited thereto since modifications may be made by those skilled in the art, particularly in light of the foregoing teachings. Reasonable variation and modification are possible within the scope of the foregoing disclosure of the invention without departing from the spirit of the invention.

What is claimed is:

1. A method for converting bar code indicia of a type selected from a plurality of bar code indicia types into a common output format comprising a standardized string of a fixed length of characters having at least two identification portions by means of a scanner and comprising the steps of:

reading the bar code indicia with the scanner;

converting the bar code indicia into an input string of a first length having at least a first portion and a second portion;

manipulating the input string into the common output format so that the length of the first string equals the fixed length of the standardized string and so that the first portion of the input string corresponds to one of the least two identification portions of the output format and the second portion of the input string corresponds to another of the at least two identification portions of the output format; and sending the first string to a processing unit.

2. A method for converting bar code indicia as recited in claim 1, further comprising the step of setting the first string to null prior to the manipulating step.

3. A method for converting bar code indicia as recited in claim 1, wherein the first length is of at least ten characters and the standardized string is of eleven characters.

4. The method for converting bar code indicia as recited in claim 1, wherein the manipulating step further includes the steps of:

identifying if the bar code indicia is of a predetermined type;

eliminating check characters from the input string; and eliminating other non-standard characters from the input string.

5. The method of converting bar code indicia as recited in claim 4, further comprising the step of comparing at least a lead character of the input string to a predetermined character.

6. The method of converting bar code indicia as recited in claim 5, wherein if the at least lead character of the input string equals the predetermined character, then comprising the additional steps of:

appending the predetermined character to the beginning of the first string; and appending at least a portion of the input string to the first string after the predetermined character.

7. The method for converting bar code indicia as recited in claim 6, wherein the lead character of the first string is zero and the characters of the input string follow the zero.

8. The method for converting bar code indicia as recited in claim 7, wherein if the input string is equal to ten characters, all the characters of the input string are added to the first string.

9. The method for converting bar code indicia as recited in claim 7, wherein if the input string is greater than ten characters, then a predetermined sequential ten of the characters of the input string is added to the first string.

10. The method for converting bar code indicia as recited in claim 9, wherein if the input string is fifteen characters, then characters four through thirteen are added to the first string.

11. The method of converting bar code indicia as recited in claim 5, wherein if the at least first character does not equal the predetermined character, then comprising the additional steps of:

comparing a first predetermined sequential group of characters of the input string starting with the lead character to a replacement predetermined sequential group of characters; and wherein if the first predetermined sequential group of the characters of the input string equal the replacement predetermined sequential group of characters, then replacing the first predetermined sequential group of characters of the input string with a substitute string of an equivalent number of characters.

12. The method or converting bar code indicia as recited in claim 11, wherein the first predetermined sequential group of the characters is five.

13. The method of converting bar code indicia as recited in claim 11, further including the step of comparing a second sequential group of the characters of the input string starting with the lead character to a predetermined sequential group of characters.

14. The method of converting bar code indicia as recited in claim 13, comprising the steps of:

appending a predetermined number of sequential characters of the input string starting with the lead character to the first string;

appending a zero to the first string after the predetermined number of sequential characters; and appending any remaining sequential characters of the input string to the first string.

15. The method of converting bar code indicia as recited in claim 14, wherein if the second sequential group of the characters of the input string equals the predetermined sequential group of characters then the initial sequential number of the characters is eight.

16. The method of converting bar code indicia as recited in claim 14, wherein if the second sequential group of the characters of the input string is not equal to the predetermined sequential group of characters then the second sequential group of the characters is five.

17. The method of converting bar code indicia as recited in claim 1, wherein the common output format comprises an NDC number commonly used in the pharmaceutical industry.

18. A method for verifying that a first and second bar code indicia are identical comprising the steps of:

reading the first bar code indicia;

converting the first bar code indicia into a standardized first string of a common output format having a predetermined length and at least a first identification portion and a second identification portion;

sending the first string to a processing unit;

storing the first string in the processing unit;

reading the second bar code indicia;

converting the second bar code indicia into a standardized second string of the common output format having the predetermined length and the at least a first identification portion and a second identification portion;

sending the second string to the processing unit;

storing the second string in the processing unit; and comparing the first string and the second string to determine whether the first and second identification portions of the first string are identical to the first and second identification portions of the second string.

19. The method of verifying bar code indicia of claim 18, comprising the step of sending a signal, the signal being a confirmation signal if the first standardized string is identical to the second standardized string and an alarm signal if the first standardized string is not identical to the second standardized string.

20. A method for converting a bar code indicia of a type selected from a plurality of bar code indicia types into a common output format comprising a standardized string of a fixed length of eleven characters having at least a first identification portion and a second identification portion by means of a scanner and comprising the steps of:

reading the bar code indicia with the scanner;

setting a standardized first string to null;

converting the bar code indicia into an input string of a first length of at least ten characters and no more than fifteen characters;

manipulating the input string into the first string so that the length of the first string equals the first length of the standardized string in the common output format, the manipulating steps comprising the sub-steps of forming the input string into the output format having the first and second identification portions by:

identifying if the bar code indicia is of a predetermined type, eliminating check characters from the input string, and eliminating other non-standard characters from the input string; and sending the standardized first string to a processing unit.

21. The method for converting a bar code indicia as recited in claim 20, comprising the further step of verifying that a first and second bar code indicia are identical and including the sub-steps of:

reading the first bar code indicia, converting the first bar code indicia into the standardized first string in the common output format, sending the first string to a processing unit, storing the first string in the processing unit, reading the second bar code indicia, converting the second bar code indicia into a standardized second string in the common output format, sending the second string to the processing unit, storing the second string in the processing unit, and comparing the first string and the second string.

22. A method for converting bar code indicia into a standardized string of a fixed length comprising characters by means of a scanner and comprising the steps of:

reading the bar code indicia with the scanner;

converting the bar code indicia into an input string of a first length;

eliminating check characters and other non-standard characters from the input string to form a first string;

comparing at least a lead character of the input string to a predetermined character, wherein if the at least lead character of the input string equals the predetermined character, then comprising the additional steps of (1) appending the predetermined character to the beginning of the first string; and (2) appending at least a portion of the input string to the first string after the predetermined character; and sending the first string to a processing unit.

23. The method of converting bar code indicia as recited in claim 22, wherein if the at least first character does not equal the predetermined character, then comprising the additional steps of:

comparing a first predetermined sequential group of characters of the input string starting with the lead character to a replacement predetermined sequential group of characters; and wherein if the first predetermined sequential group of the characters of the input string equal the replacement predetermined sequential group of characters, then replacing the first predetermined sequential group of characters of the input string with a substitute string of an equivalent number of characters.

24. The method or converting bar code indicia as recited in claim 23, wherein the first predetermined sequential group of the characters is five.

25. The method of converting bar code indicia as recited in claim 23, further including the step of comparing a second sequential group of the characters of the input string starting with the lead character to a predetermined sequential group of characters.

26. The method of converting bar code indicia as recited in claim 25, comprising the steps of:

appending a predetermined number of sequential characters of the input string starting with the lead character to the first string;

appending a zero to the first string after the predetermined number of sequential characters; and appending any remaining sequential characters of the input string to the first string.

27. The method of converting bar code indicia as recited in claim 26, wherein if the second sequential group of the characters of the input string equals the predetermined sequential group of characters then the initial sequential number of the characters is nine.

28. The method of converting bar code indicia as recited in claim 26, wherein if the second sequential group of the characters of the input string is not equal to the predetermined sequential group of characters then the second sequential group of the characters is five.

29. The method for converting bar code indicia as recited in claim 22, wherein the lead character of the first string is zero and the characters of the input string follow the zero.

30. The method for converting bar code indicia as recited in claim 29, wherein if the input string is equal to ten characters, all the characters of the input string are added to the first string.

31. The method for converting bar code indicia as recited in claim 29, wherein if the input string is greater than ten characters, then a predetermined sequential ten of the characters of the input string is added to the first string.

32. The method for converting bar code indicia as recited in claim 31, wherein if the input string is fifteen characters, then characters four through thirteen are added to the first string.

33. A method for converting a bar code indicia representing a bar code of a first type selected from a group of a plurality of bar code types containing a first predetermined number of characters to a NDC string containing a second predetermined number of characters including a first source identification portion, a second product identification portion and a third trade package portion by means of a scanner and comprising the steps of:

reading the bar code indicia with the scanner;

converting the bar code indicia into an input string representing the bar code of the first predetermined number of characters;

extracting a first subset of characters from the input string corresponding to the first source identification portion;

extracting a second subset of characters from the input string corresponding to the second product identification portion;

extracting a third subset of characters from the input string corresponding to the trade package portion;

forming a second string by combining the first source identification, second product identification and third trade package portions of a length equal to the second predetermined number of characters; and sending the second string to a processing unit.

34. A method for converting bar code indicia as recited in claim 33, wherein the first predetermined number of characters is at least ten characters and the second predetermined number of characters is eleven characters.

35. The method for converting bar code indicia as recited in claim 33, and further comprising the step of:

identifying which type of the group of bar code formats is the bar code indicia; and eliminating check characters and other non-standard characters from the input string based upon the type of bar code indicia.

36. The method of converting bar code indicia as recited in claim 33, and further comprising the step of comparing at least a lead character of the input string to a predetermined character.

37. The method of converting bar code indicia as recited in claim 36, wherein if the at a least lead character of the input string equals the predetermined character, then comprising the additional steps of:

appending the predetermined character to the beginning of the second string; and appending at least a portion of the input string to the second string after the predetermined character to form at least one of the first source identification, second product identification and third trade package portions of the second string.

38. A method for converting bar code indicia of a type selected from a plurality of bar code types into a standardized string of a fixed length of characters by means of a scanner and comprising the steps of:

reading the bar code indicia with the scanner;

converting the bar code indicia into an input string of an input length of characters;

manipulating the input string to reflect a root string of a root string length of characters depending upon at least one of the type of bar code indicia, the input length and the type of characters comprising the input string;

comparing a first predetermined number of characters of the root string with a first identifier string; and creating an output string comprising at least one insert character and the root string based upon the result of the comparing step.

39. The method of converting bar code indicia as recited in claim 38, wherein if the first predetermined number of characters of the root string equals the first identifier string then the step of creating the output string comprises appending the root string to the at least one insert character.

40. The method of converting bar code indicia as recited in claim 38, wherein if the first predetermined number of characters of the root string does not equal the first identifier string then a second predetermined number of characters is compared to a list comprising at least one string having an equal number of characters as the second predetermined number of characters.

41. The method of converting bar code indicia as recited in claim 40, wherein the second predetermined number of characters is five characters.

42. The method of converting bar code indicia as recited in claim 40, wherein each of the at least one string in the list corresponds to a manufacturer identification code.

43. The method of converting bar code indicia as recited in claim 40, wherein if the second predetermined number of characters of the root string is found in the list, then the step of creating the output string comprises one of a third predetermined number of characters of the root string and a substitute string having the third predetermined number of characters and having the at least one insert character and a remainder of the characters of the root code appended thereto.

44. The method of converting bar code indicia as recited in claim 43, wherein the third predetermined number of characters is eight characters.

45. The method of converting bar code indicia as recited in claim 40, wherein if the second predetermined number of characters of the root string is not found in the list, then the step of creating the output string comprises a fourth predetermined number of characters of the root string having the at least one insert character and a remainder of the characters of the root code appended thereto.

46. The method of converting bar code indicia as recited in claim 45, wherein the fourth predetermined number of characters is five characters.

47. The method of converting bar code indicia as recited in claim 38, wherein the first identifier string comprises a "zero" character.

48. The method of converting bar code indicia as recited in claim 38, wherein the root code length is ten characters.

49. The method of converting bar code indicia as recited in claim 38, wherein the fixed length of characters is eleven characters.

50. The method of converting bar code indicia as recited in claim 38, wherein the output string represents an NDC number as commonly referred to in the pharmaceutical industry.

51. The method of converting bar code indicia as recited in claim 38, wherein the first predetermined number of characters comprises one character.

* * * * *

UNITED STATES PATENT AND TRADEMARK OFFICE
CERTIFICATE OF CORRECTION

PATENT NO. : 6,098,892
DATED : August 8, 2000
INVENTOR(S) : Max J. Peoples Jr.

It is certified that error appears in the above-identified patent and that said Letters Patent is hereby corrected as shown below:

Column 1, claim 38,
Lines 11-12, "a root string of a root string length" should read -- a root string of a length --.

Signed and Sealed this

Twentieth Day of November, 2001

Attest:

Nicholas P. Godici

NICHOLAS P. GODICI
*Acting Director of the United States Patent and Trademark Office*

*Attesting Officer*